(12) United States Patent
Biedermann et al.

(10) Patent No.: US 11,963,701 B2
(45) Date of Patent: Apr. 23, 2024

(54) SYSTEM OF A ROD INSERTION DEVICE AND A ROD

(71) Applicant: BIEDERMANN TECHNOLOGIES GMBH & CO. KG, Donaueschingen (DE)

(72) Inventors: Timo Biedermann, Trossingen (DE); Achim Schünemann, Villingen-Schwenningen (DE); Tobias Hägle, Donaueschingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/393,760

(22) Filed: Aug. 4, 2021

(65) Prior Publication Data

US 2022/0039845 A1 Feb. 10, 2022

Related U.S. Application Data

(60) Provisional application No. 63/060,860, filed on Aug. 4, 2020.

(30) Foreign Application Priority Data

Aug. 4, 2020 (EP) .................................... 20189382

(51) Int. Cl.
*A61B 17/70* (2006.01)
(52) U.S. Cl.
CPC ...... *A61B 17/7088* (2013.01); *A61B 17/7004* (2013.01); *A61B 17/701* (2013.01)
(58) Field of Classification Search
None
See application file for complete search history.

(56) References Cited

U.S. PATENT DOCUMENTS 9,539,034 B2 1/2017 Biedermann et al.
2005/0090824 A1* 4/2005 Shluzas .............. A61B 17/7083
606/279

(Continued)

FOREIGN PATENT DOCUMENTS

WO WO 2016/077208 A1 5/2016

OTHER PUBLICATIONS

Extended European Search Report for Application No. 20189382.3, dated Feb. 10, 2021, 12 pages.
Nuvasive, Reline Technique Guide, 2018, 140 pages.

*Primary Examiner* — Tessa M Matthews
(74) *Attorney, Agent, or Firm* — Lewis Roca Rothgerber Christie LLP

(57) ABSTRACT

A system for spine surgery includes a rod with a longitudinal axis and a connection portion, and a rod insertion device including a rod holding member with a central axis and a rod engagement portion, wherein at least part of a shape of the rod engagement portion substantially matches at least part of a shape of the connection portion to engage the connection portion in a fixed manner at more than one distinct rotational orientation around the longitudinal axis. When the connection portion is engaged with the rod engagement portion, when viewed in a plane perpendicular to the longitudinal axis, a cross-section of the connection portion has a maximum height measured in a direction of the central axis of the rod holding member that is greater than a maximum width of the connection portion measured in a direction transverse to the longitudinal axis.

21 Claims, 16 Drawing Sheets

(56) References Cited

U.S. PATENT DOCUMENTS

| | | | |
|---|---|---|---|
| 2008/0312703 A1* | 12/2008 | Hestad | A61B 17/7085 |
| | | | 606/86 A |
| 2009/0105774 A1* | 4/2009 | Jones | A61B 17/7083 |
| | | | 606/86 A |
| 2010/0222828 A1* | 9/2010 | Stad | A61B 17/7083 |
| | | | 606/279 |
| 2014/0277166 A1* | 9/2014 | Brinkman | A61B 17/7086 |
| | | | 606/279 |
| 2017/0020584 A1 | 1/2017 | Smith | |
| 2017/0238975 A1* | 8/2017 | Doose | A61B 17/7088 |

* cited by examiner

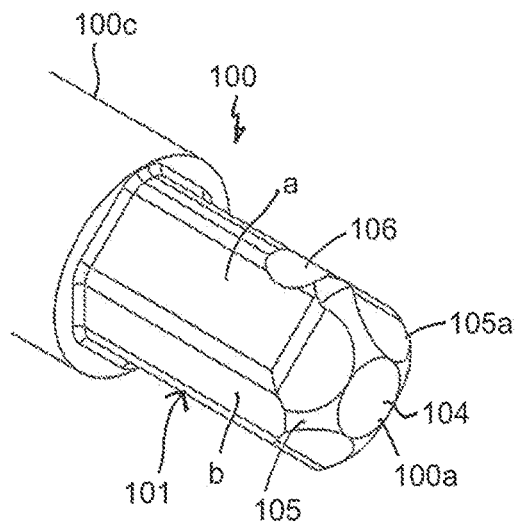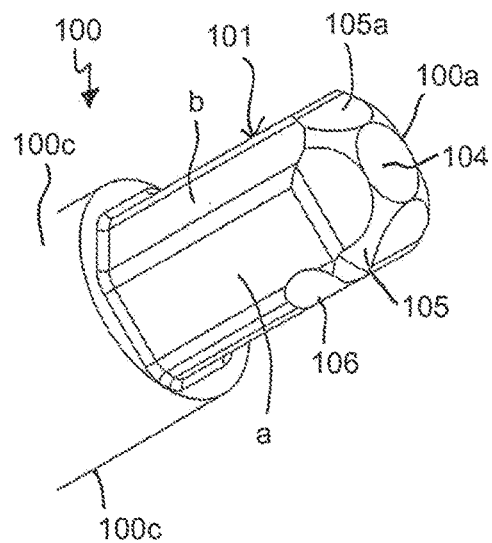
Fig. 5               Fig. 6
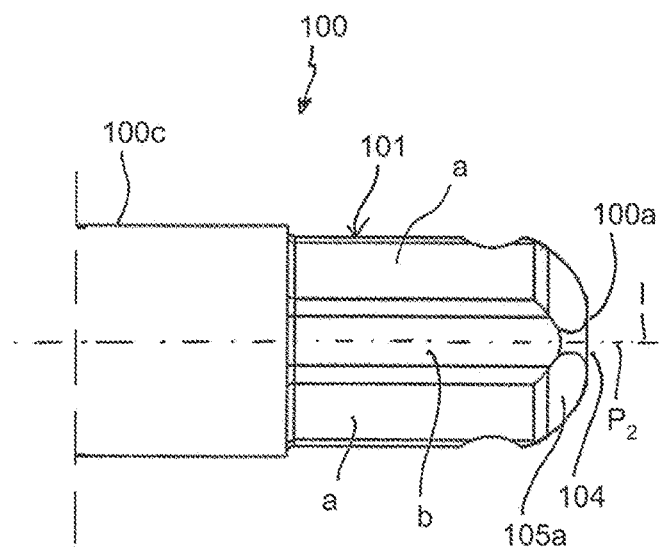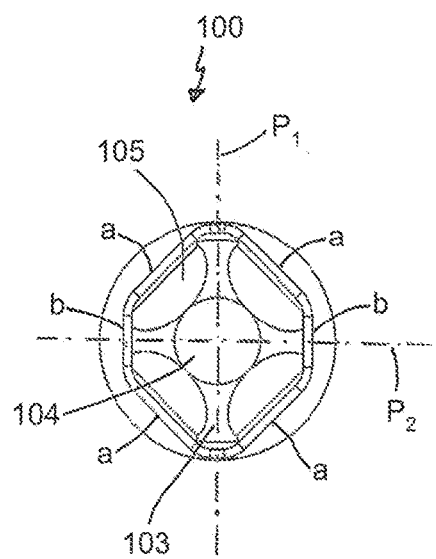
Fig. 7               Fig. 8

SYSTEM OF A ROD INSERTION DEVICE AND A ROD

CROSS-REFERENCE TO RELATED APPLICATION(S)

The present application claims priority to and the benefit of U.S. Provisional Patent Application No. 63/060,860, filed Aug. 4, 2020, the contents of which are hereby incorporated by reference in their entirety, and claims priority from European Patent Application EP 20 189 382.3, filed Aug. 4, 2020, the contents of which are hereby incorporated by reference in their entirety.

BACKGROUND

Field

The application relates to a system including a rod insertion device and a rod. Such a system is particularly useful in spine surgery, and more particularly in minimally invasive spine surgery.

Description of Related Art

In minimally invasive surgery (MIS), only small incisions are made, and therefore the available space for surgical manipulations is reduced. This may also be the case in other fields of spine surgery, such as cervical spine surgery or pediatric spine surgery. Hence, there exists a specific demand to cope with the reduced available space.

A rod insertion device and a rod that are particularly suitable for MIS applications are described, for example, in U.S. Pat. No. 9,539,034 B2. The rod insertion device includes a shaft with a rod holding member for holding the rod, wherein the rod holding member is connected to a first end of the shaft and configured to pivot relative to the shaft. A detent member is configured to selectively engage the rod holding member to latch a pivot position of the rod holding member relative to the shaft.

A minimally invasive spinal fixation system and related methods are described in US 2017/0238975 A1. The spinal rod described there includes a first end that is generally rounded and a second end that is configured to engage a rod inserter. The spinal rod includes a post having a shape corresponding to the shape of the rod cavity on the rod inserter. The post includes a recess formed on an upper surface of the post and configured to receive the distal lip of a locking member on the rod inserter to temporarily secure the rod to the rod inserter. The rod inserter includes an outer sleeve with a rod holder pivotally attached to the distal end of the outer sleeve and including a rod cavity configured to receive the post of the spinal rod. A pivoting and locking mechanism is provided, permitting the rod inserter to introduce the spinal rod at one angle, and then pivoting of the rod.

SUMMARY

It is an object of the invention to provide a rod insertion device, a rod, and a system including a rod insertion device and a rod that provides for an improved or alternative way of treating various spine disorders, conditions, and/or diseases through a bone anchor and rod construct. Moreover, a method for engaging a rod by a rod insertion device shall be provided.

In an embodiment, a system including a rod insertion device and a rod, in particular for spine surgery, may include a rod having a connection portion with an outer contour around a longitudinal axis of the connection portion, and a rod insertion device including a rod holding member with a rod engagement portion at one end thereof configured to engage the connection portion of the rod, wherein the connection portion has a cross-section in a plane perpendicular to the longitudinal axis, the cross-section having a vertical axis and a horizontal axis perpendicular to the vertical axis, and wherein a maximum height of the connection portion is greater than a maximum width, and the maximum height lies substantially in the direction of the vertical axis, and wherein the rod engagement portion has an inner contour which substantially matches at least a portion of the outer contour of the connection portion so that the connection portion is engageable by the rod engagement portion in a form-fit manner with respect to a rotation around the longitudinal axis.

With such a design, the overall width of the rod engagement portion, and in turn of the entire rod insertion device, can be made relatively slim without losing strength. Preferably the connection portion has a polygonal outer contour and more preferably a hexagonal outer contour with two pairs of long sides and a short side between each pair of long sides. Further preferably, the shape of the connection portion is substantially that of a prism. One longitudinal edge of the prism is facing the rod insertion device, and the rod insertion device is configured to engage the connection portion on two substantially adjacent sides from above and two substantially adjacent sides from below. This results in a higher strength connection.

In addition with such a design, the connection portion can be sized sufficiently large such that it can be re-engaged easily by the rod insertion device for repositioning or other correction steps which require a re-attachment to the rod once it has been placed. Moreover the connection portion is easy to manufacture.

In another embodiment, a system including a rod insertion device and a rod, in particular for spine surgery, may include a rod having a connection portion with a polygonal outer contour around a longitudinal axis of the connection portion, and a rod insertion device including a rod holding member with a rod engagement portion at one end thereof configured to engage the connection portion of the rod, wherein the rod engagement portion is shaped such that the connection portion is engageable and fixable in a first position of the rod and in a second position of the rod in which the rod is rotated by 180°.

The first position and the second position are the only positions in which the rod is fixable by the rod insertion device. Hence, the positions in which the rod can be engaged by the rod insertion device are clearly defined. In the case of a rod with properties that depend on the orientation in which the rod is inserted, the rod can be easily pre-oriented while the rod is engaged in the desired rotational position with the rod insertion device. This is particularly useful for curved rods that are used to treat kyphosis or lordosis. The required direction of the curvature can be easily selected at the step of inserting the rod.

The interconnection between the rod and the rod insertion device in the embodiments is simple, versatile, and robust. Moreover the shape of the connection portion is such that other instruments, such as a drive tool, can be attached to the connection portion of the rod, for example a ring wrench, that allows rotation of the rod once the rod has been inserted into the rod channel of a bone anchor. Preferably, the rotation can be effected in steps of 45°.

A plurality of rods with different diameters or different shapes, straight rods, curved rods, etc., can be equipped with the same connection portion which has in each case the same size and shape. Therefore, it is possible to use the rod insertion device in combination with a plurality of different rods.

In addition, it is possible to selectively connect various rod insertion devices to the rod. In one specific embodiment, the rod insertion device is relatively slim around the vertical axis so that the insertion device can be inserted and removed between the rod channel of a bone anchor or between extended tabs that may be used in MIS to extend the rod channel of a bone anchor. In another specific embodiment, the rod insertion device can be removed in a vertical direction relative to the rod, which requires less space compared to a removal along the axis of the rod.

As used in the present specification and the appended claims, the term "rod" shall be understood as including any elongate member, regardless of the cross-sectional shape. Specifically, a spinal stabilization rod as used herein, may have substantially circular, oval, or angular cross-sections. Such cross-sections may also vary along the length of the rod.

BRIEF DESCRIPTION OF THE DRAWINGS

Further features and advantages of the invention will become apparent from the description of embodiments by means of the accompanying drawings. In the drawings:

FIG. 5 shows a perspective view from a top of a connection portion of the rod of FIGS. 3 and 4.

FIG. 6 shows a perspective view from a bottom of the connection portion of FIG. 5.

FIG. 7 shows a side view of the connection portion of FIGS. 5 and 6.

FIG. 8 shows a front view of the connection portion of FIGS. 5 to 7.

DETAILED DESCRIPTION

Figures 1, 2:
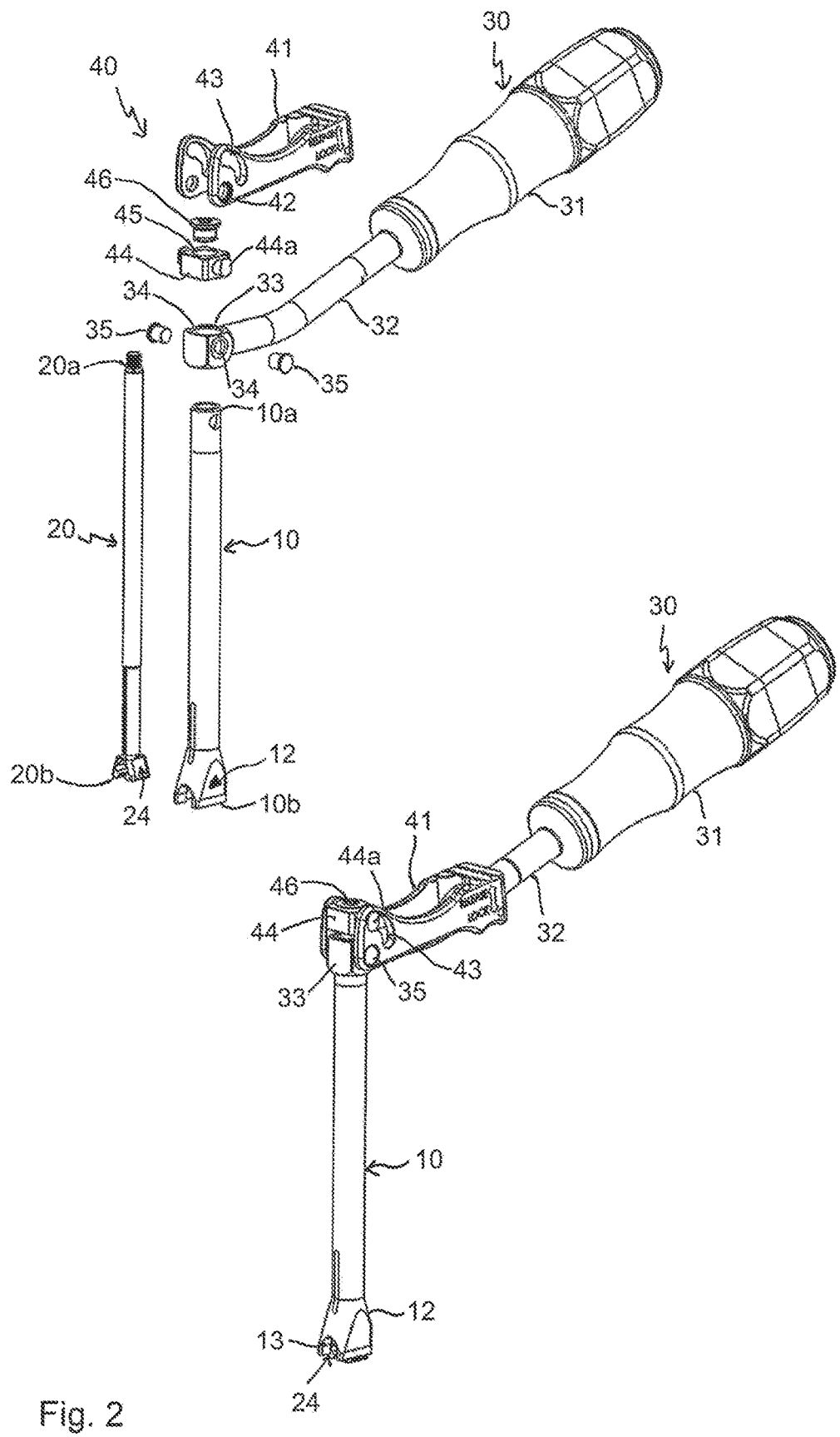
FIG. 1 shows a perspective exploded view of a rod insertion device according to a first embodiment.
FIG. 2 shows a perspective view of the rod insertion device of FIG. 1 in an assembled state.

With respect to FIGS. 1 and 2, the rod insertion device includes an outer sleeve 10 that is configured to receive a rod holding member 20, which is movable in an axial direction relative to the outer sleeve 10. The outer sleeve 10 is connected at a rear end 10a to a handle 30 for holding the rod insertion device. A front end 20b of the rod holding member 20 includes a rod engagement portion 24 as described below. The outer sleeve 10 also has a front end 10b with a portion 12 that forms a housing for the rod engagement portion 24.

The handle 30 includes a gripping portion 31, which is connected through a bar 32 to a handle connection portion 33 for connecting the gripping portion 31 to the outer sleeve 10. The handle connection portion 33 has a through-hole 34 with an axis that is substantially perpendicular to the longitudinal axis of the gripping portion 31 for connecting the handle connection portion 33 to a rear end 10a of the outer sleeve 10 through pins 35. A displacement mechanism 40 for moving, more specifically for displacing, the rod holding member 20 relative to the outer sleeve 10 includes a fork-shaped bracket 41, which is attached through the pins 35 extending through holes 42 at the free ends of the bracket 41 to the handle connection portion 33 and to the rear end 10a of the outer sleeve 10 in a pivotable manner. Above the holes 42, oblong curved holes 43 are provided on the free ends of the bracket 41, respectively, which are configured to receive and to guide pin-like extensions 44a of a connection piece 44 of the displacement mechanism 40. The connection piece 44 has a through-hole 45 perpendicular to the axis of the extensions 44a, that receives a sleeve 46 therein which has an inner thread configured to connect to an outer thread at a rear end 20a of the rod holding member 20, so that the rod holding member 20 can be fixedly connected to the connecting piece 44 via the sleeve 46.

In the assembled state as shown in FIG. 2, the handle 30 extends substantially perpendicular to the outer sleeve 10. When the bracket 41 is in a lock position, the bracket extends substantially in the direction of the bar 32 of the handle 30 and the extensions 44a are in an uppermost corner of the elongate oblong hole 43. The front end 20b of the rod holding member 20 is within the outer sleeve 10 in the retracted position as shown, for example in FIGS. 19 to 22, where the rod holding member 20 locks an engaged rod. When the bracket 41 is moved to a release position by pivoting around the pins 35, the extensions 44a are guided in the oblong holes 43, respectively, so that the rod holding member 20 is displaced relative to the outer sleeve 20 until the rod engagement portion 24 projects out of the front end 10b of the outer sleeve 10, as shown in FIGS. 15 to 18. In the release position, the bracket 41 extends substantially in the direction along the length of the outer sleeve 10. Hence, by pivoting the bracket 41, the rod holding member 20 can be displaced relative to the outer sleeve 10 to receive/release or to lock the rod.

It shall be noted that the connection between the rod holding member and the outer sleeve through the displacement mechanism shown is only exemplary. Other displacement mechanisms and connections can be used for permitting a relative movement between the rod holding member 20 and the outer sleeve 10.

Figure 3:
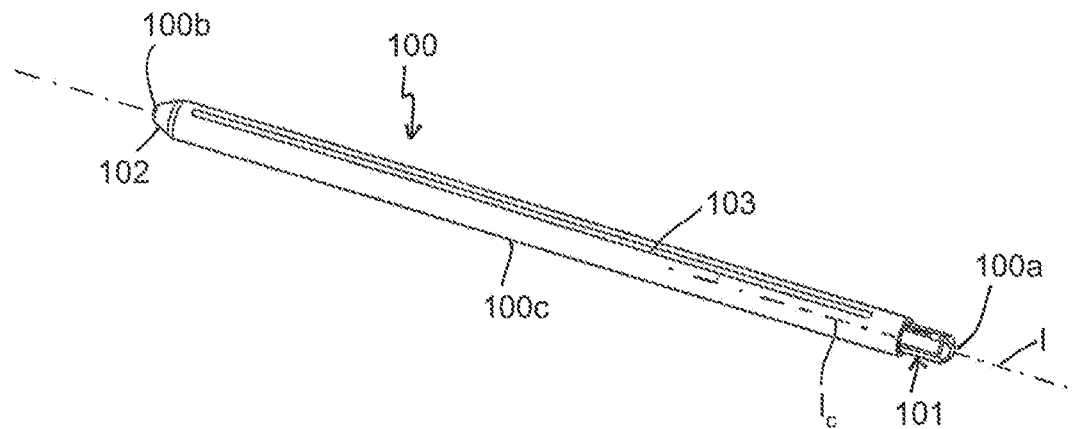
FIG. 3 shows a perspective view of a first embodiment of a rod configured to be inserted with the rod insertion device of FIGS. 1 and 2.
Figure 4:
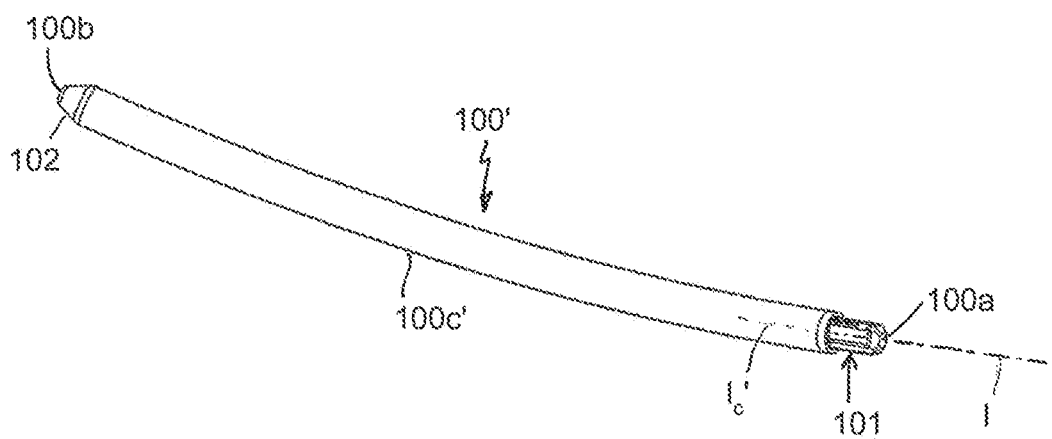
FIG. 4 is a perspective view of a second embodiment of a rod configured to be inserted with the rod insertion device of FIGS. 1 and 2.

Referring to FIGS. 3 and 4, two types of rods are shown. FIG. 3 depicts a straight rod 100 with a first end 100a and an opposite second end 100b. A main portion 100c of the rod is cylindrical. The surface of the rod may be smooth. Adjacent to the first end 100a, a connection portion 101 is formed for connecting the rod 100 to the rod insertion device. The connection portion 101 defines a longitudinal axis l that is in the case of the straight rod coincident with a cylinder axis $l_c$ of the rod. A largest width of the connection portion 101 in a direction perpendicular to the longitudinal axis l may be the same or smaller than the diameter of the rod at the junction between the connection portion 101 and the main part 100c. At the second end 100b, a tapered tip portion 102, preferably with a rounded end, may be provided. Furthermore, a marking 103, for example a line extending parallel to the cylinder axis of the rod, may be provided on the outer surface, which serves for orienting the rod 100, more specifically for orienting the connection portion 101, correctly with respect to the rod insertion device.

The rod 100', as shown in FIG. 4, is a curved rod that has a circular cross-section and a curvature along its length in the main portion 100c. The connection portion 101 of this rod is identical to the connection portion 101 of the rod 100. Also the tip portion 102 may be identical to that of the straight rod 100. The longitudinal axis l of the connection portion 101 is straight, whereas a central axis $l_c'$ through the main portion is curved. Also the curved rod 100' may have a marking 103 to indicate the orientation of the rod 100'.

It shall be noted that the longitudinal axis of the connection portion 101 and the central axis of the main portion in both rods shown in the figures are coincident at the junction between the main portion 100c and the connection portion. However, they may also be offset from each other in other embodiments.

The connection portion 101 will now be described, referring to FIGS. 5 to 8. Generally, the connection portion 101 defines an outer contour that is substantially the same for all connection portions of other rods that shall be used together with the rod insertion device. A length of the connection portion 101 is such that the connection portion is suitable to be engaged by the engagement portion 24 of the rod holding member 20. The contour of the outer surface of the connection portion 101 around the longitudinal axis is such that it is mirror-symmetrical with respect to a first plane $P_1$ that includes the longitudinal axis l and goes through the center of the marking 103 (FIG. 2) in the length direction, and is also mirror-symmetrical with respect to a second plane $P_2$ extending at an angle of 90° to the first plane $P_1$, as can be seen in particular in FIG. 8. In a cross-section perpendicular to the longitudinal axis l, the plane $P_1$ defines a vertical axis and the plane $P_2$ defines a horizontal axis. More specifically, the outer contour of the connection portion 101 is polygonal, and in particular hexagonal. When seen in the cross-section perpendicular to the longitudinal axis l, the outer contour includes four long sides a, wherein each long side forms an angle of about 45° with the plane $P_1$ so that the long sides of each pair of long sides form an angle of about 90° with each other. The two pairs of long sides a are connected by short sides b, respectively, that are shorter than the long sides and are substantially parallel to the plane $P_1$. The transition portions, i.e. the edges of the polygon, between two adjacent long sides a and the transition portions between a long side a and a short side b may be rounded. In other words, in the cross-section, four equal long sides a form a diamond-shaped or lozenge-shaped envelope, which may also be considered substantially square-shaped. Generally the maximum height of the connection portion lies in the vertical axis, and the maximum height is greater than the maximum width. The cross-section of the connection portion 101 is substantially constant over a length along the longitudinal axis l that is sufficient for engagement by the rod insertion device. Thus, the overall shape of the connection portion 101 is that of a prism, at least in the region that is to be engaged by the rod insertion device.

The contour may be manufactured, for example, by cutting away material from two sides of a four-cornered end portion to generate the short sides b. It shall be noted that while the long sides a and the short sides b are shown as flat sides, they may also be outwardly or inwardly curved with respect to the longitudinal axis l.

Preferably, the outer end of the connection portion 101 may be chamfered to avoid sharp edges. As can be seen in the Figures, the connection portion 101 may have a flat end 104 and a spherical-segment-shaped section 105 between the polygonal structure and the flat end 104. The continuation sections 105a of the long sides a which extend into the spherical-segment shaped portion 105 may be conically tapered and may have circular ends. However, it shall be noted that the shapes and structures of these portions may vary according to the machining process and other conditions.

In addition, there may be two transverse recesses 106 provided in the polygonal outer surface of the connection portion 101 which are offset by 180° and located between two adjacent long sides a. In other words, the recesses 106 intersect the plane $P_1$ between the adjacent long sides a. The shape of the recesses 106 may be cylindrical with a cylinder axis perpendicular to the longitudinal axis l of the connection portion. By means of this, an engagement member such as a transverse pin can engage one of the recesses to provide additional fixation.

The connection portion 101 is configured to be engaged by an engagement portion 24 of the rod holding member 20 in a first position in which one pair of long sides a is facing the engagement portion 24 and the other pair of long sides a is facing away from the engagement portion 24. Similarly, the connection portion 101 can be engaged by the engagement portion in a second position in which the opposite pair of long sides a faces towards the connection portion, i.e. when the rod is rotated by 180° around the longitudinal axis l.

Figures 9, 10:
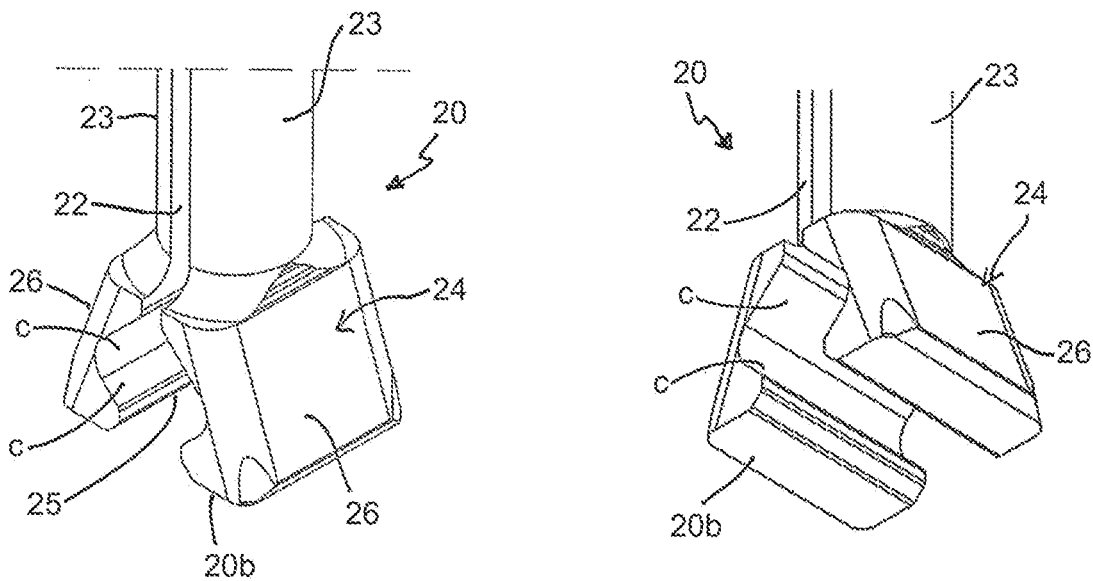
FIG. 9 shows a perspective view from a top of a front end of a rod holding member of the rod insertion device of FIGS. 1 and 2.
FIG. 10 shows a perspective view from a bottom of the rod holding member of FIG. 9.
Figure 11:
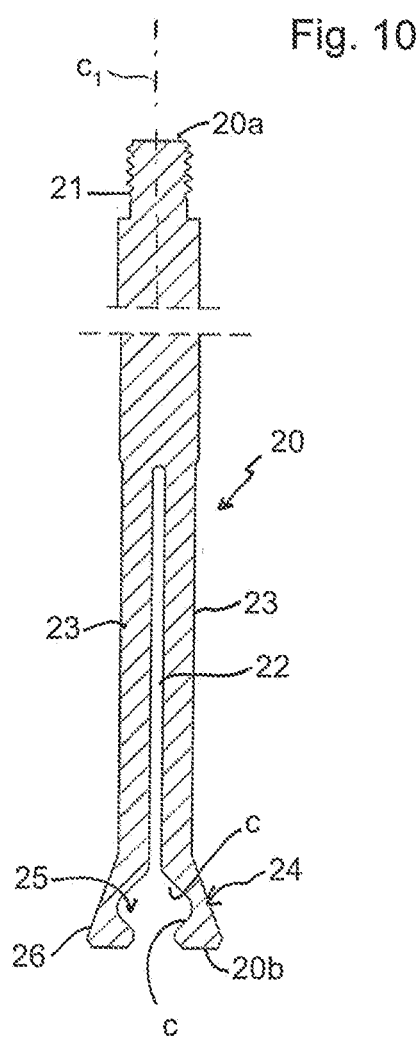
FIG. 11 shows a cross-sectional view of the rod holding member of FIGS. 9 and 10, the cross-section taken in a plane extending through a center of the rod holding member and perpendicular to a rod axis of a held rod.

Next, the rod holding member 20 will be described in greater detail, referring to FIGS. 9 to 11. The rod holding member 20 is a substantially elongate rod-like member which includes the threaded portion 21 at its rear end 20a that may have a smaller diameter than the rest of the rod holding member 20, so that the rod holding member 20 can be firmly connected to the connection piece 44. The thread axis of the threaded end portion 21 defines a central longitudinal axis $c_1$ of the rod holding member 20. By means of a slot 22 extending from the front end 20b to a distance from the rear end 20a, two arms 23 are formed which can be resiliently compressed towards each other and spread apart from each other. The length of the slot 22 is such that the arms 23 exhibit a sufficient flexibility. For example, the length of the slot 22 may extend over half or more than half of the total length of the rod holding member 20. Adjacent to the front end 20b, the rod engagement portion 24 is formed that has a rod receiving cavity 25. The rod receiving cavity 25 is open towards the front end 20b to permit placing the rod engagement portion 24 over the connection portion 101 of the rod 100. Due to the flexibility of the arms 23, the connection portion 101 can snap into the cavity 25. An inner contour of the rod receiving cavity 25 preferably matches an outer contour of the connection portion 101 in the region of the long sides a. More specifically, the inner contour of the rod engagement portion 24 is hollow polygonal, however, with only four engagement surfaces c that are arranged in a substantially diamond-like arrangement when seen in cross-section or from the front. Hence, planes defined by each of the engagement surfaces c intersect the longitudinal axis $c_1$.

Figure 20:
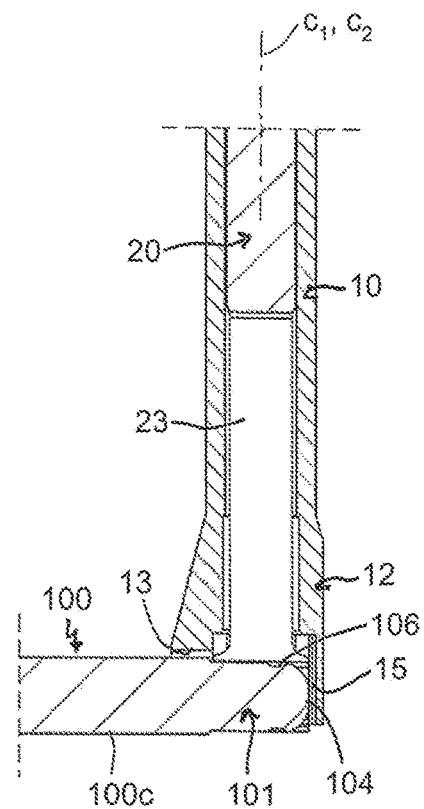
FIG. 20 shows a cross-sectional view of the rod and the rod insertion device of FIG. 19, with the rod engaged by the rod insertion device, the cross-section extending through a center of the rod and through a center of the rod insertion device.
Figure 21:
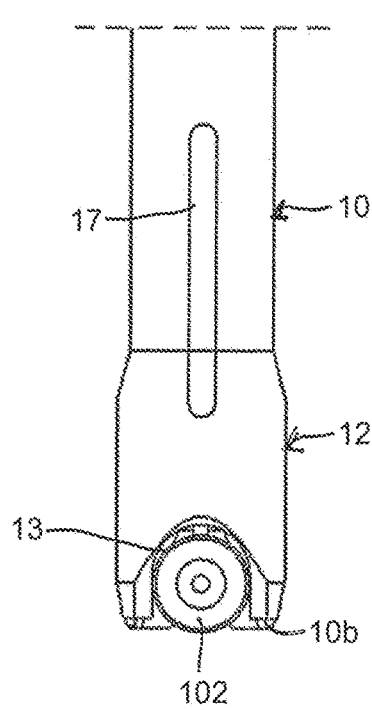
FIG. 21 shows a front view of the rod and the rod insertion device of FIGS. 19 and 20, with the rod engaged by the rod insertion device, seen from a second end of the rod opposite to the connection portion.

A length of the rod receiving cavity 25 in a direction perpendicular to the central longitudinal axis $c_1$ of the rod holding member 20 is such that, when the rod engagement portion 25 is placed onto the connection portion 101, the rod receiving cavity 25 extends substantially along the whole length of the connection portion 101, as can be seen in FIG. 20, for example. An outer surface 26 of the rod engagement portion 24 is preferably outwardly tapered, i.e., widens towards the front end 20b. By means of this, when the rod holding member 20 is retracted in the outer sleeve 10, an increasing pressure can be exerted onto the tapered outer surface 26 of the rod engagement portion 24, which results in compression of the rod receiving cavity 25.

Figure 18:
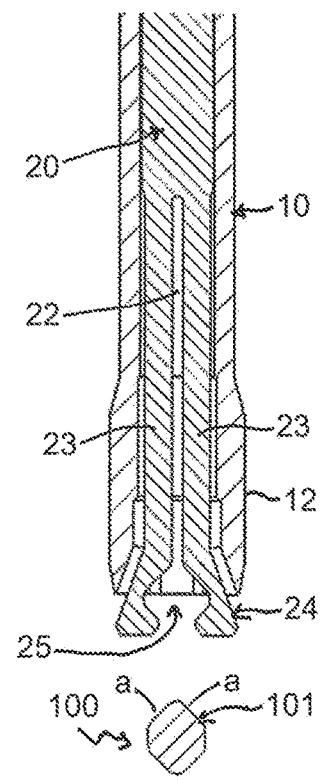
FIG. 18 shows a cross-sectional view of the rod and rod insertion device of FIGS. 15 to 17, the cross-section taken in a plane perpendicular to the rod axis and extending through a center of the rod insertion device.
Figure 19:
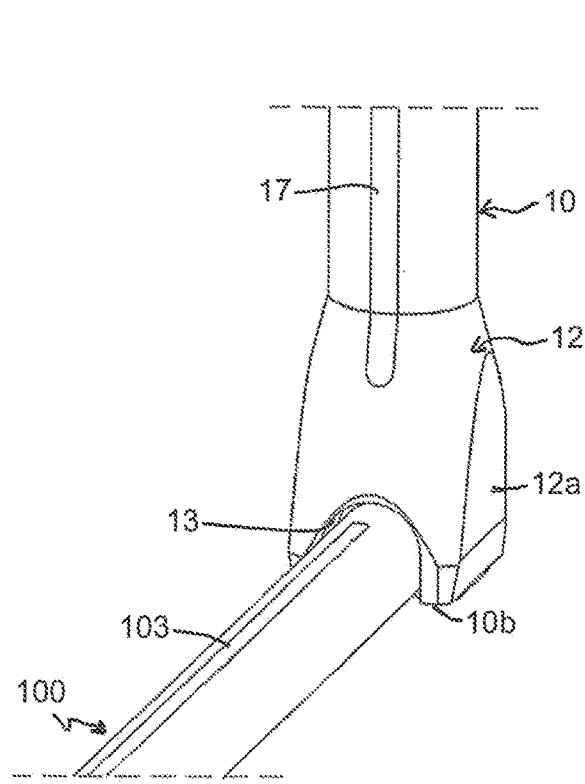
FIG. 19 shows a perspective view of the rod and the rod insertion device of FIGS. 15 to 18, but with the rod engaged by the rod insertion device.
Figure 22:
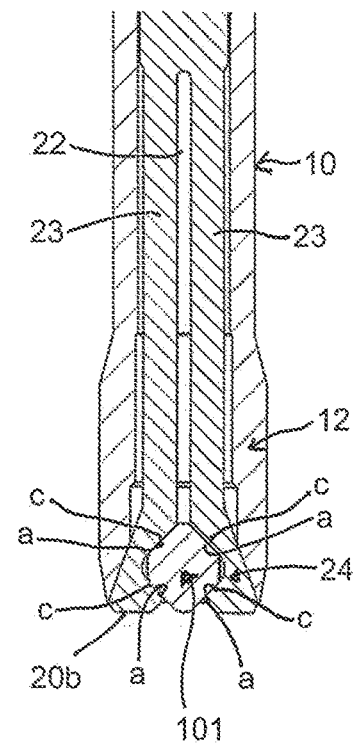
FIG. 22 shows a cross-sectional view of the rod and the rod insertion device of FIGS. 19 to 21, with the rod engaged by the rod insertion device, the cross-section taken in a plane perpendicular to the rod axis and extending through a center of the rod insertion device.

The axial length of the rod holding member 20 is such that in the release position the rod engagement portion 24 protrudes with at least a portion of the cavity 25 out of the front end 10b of the outer sleeve 10, as shown in FIG. 18. In the locking position when the rod holding member 20 is retracted, the rod engagement portion 24 projects only slightly or does not project out of the front end 10b of the outer sleeve 10, as shown in FIG. 22.

Figures 12, 13:
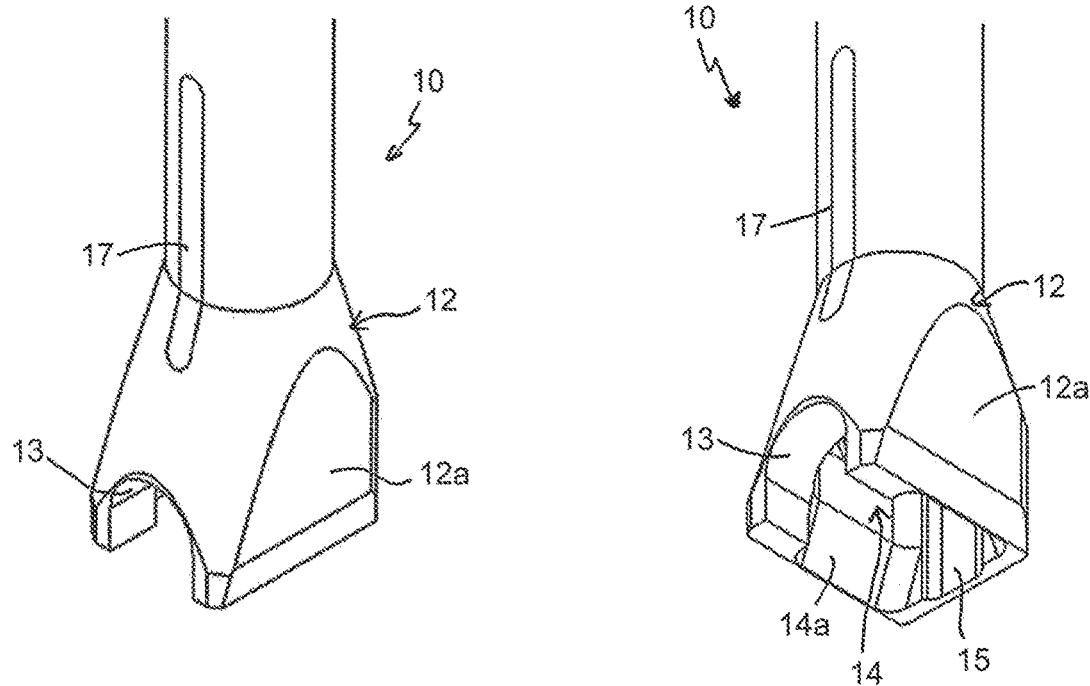
FIG. 12 shows a perspective view from a top of a front portion of an outer sleeve of the rod insertion device of FIGS. 1 and 2.
FIG. 13 shows a perspective view from a bottom of the outer sleeve of FIG. 12.
Figure 14:
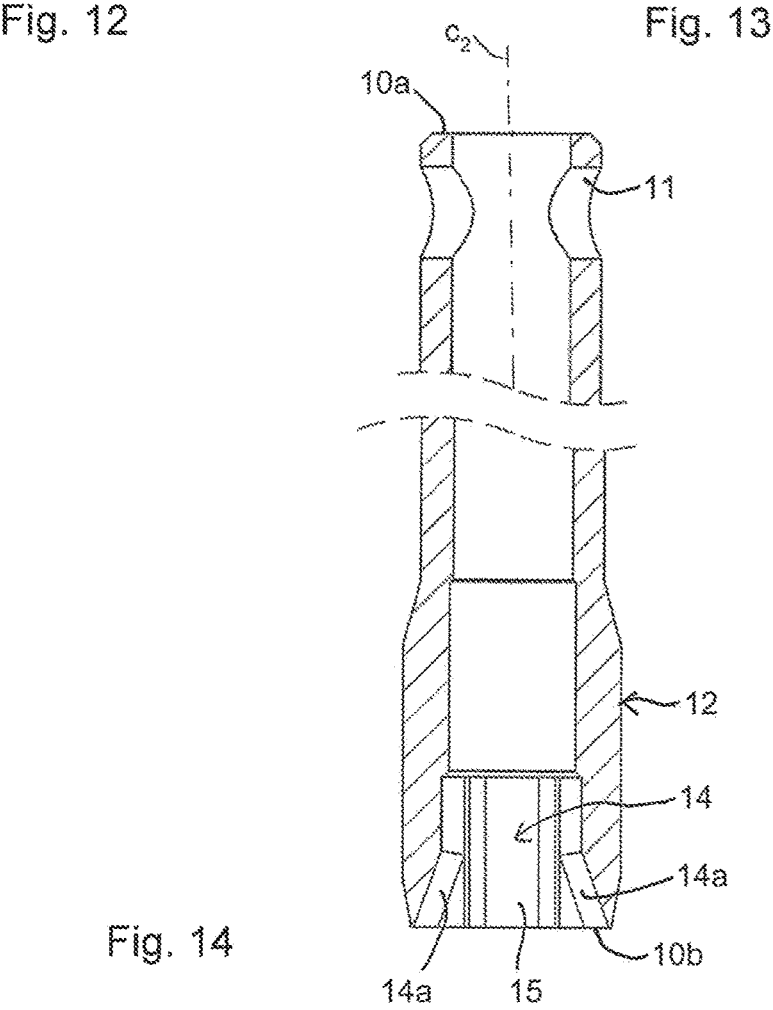
FIG. 14 shows a cross-sectional view of the outer sleeve of FIGS. 12 and 13, the cross-section taken in a plane through the center of the outer sleeve and perpendicular to the rod axis.
Figure 15:
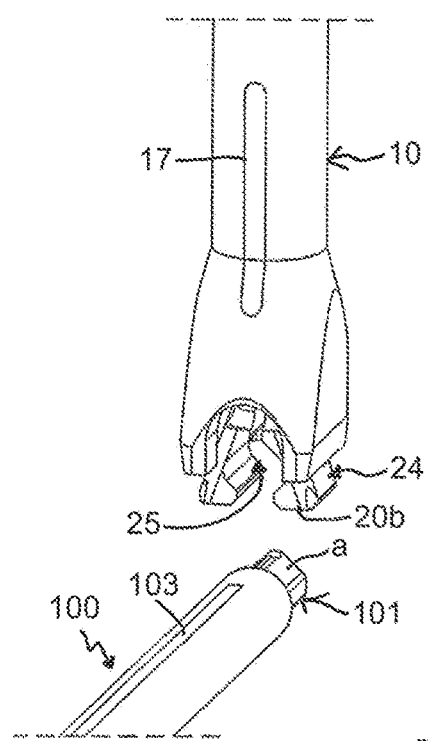
FIG. 15 shows a perspective view of a front portion of the rod of FIG. 3 and the rod insertion device of FIGS. 1 and 2, where the rod is not engaged.
Figure 16:
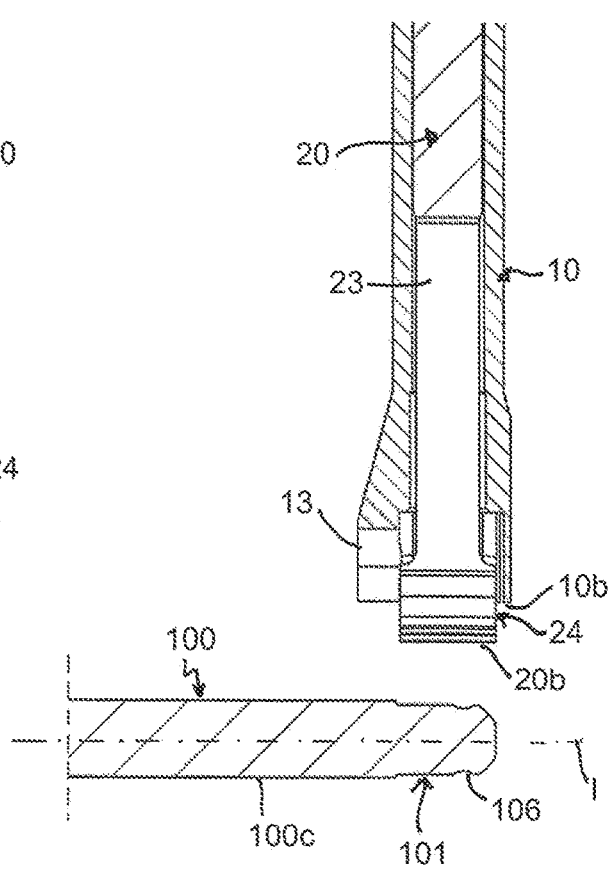
FIG. 16 shows a cross-sectional view of the rod and the rod insertion device of FIG. 15, the cross-section extending through a center of the rod in the length direction along the rod axis and through a center of the rod insertion device.
Figure 17:
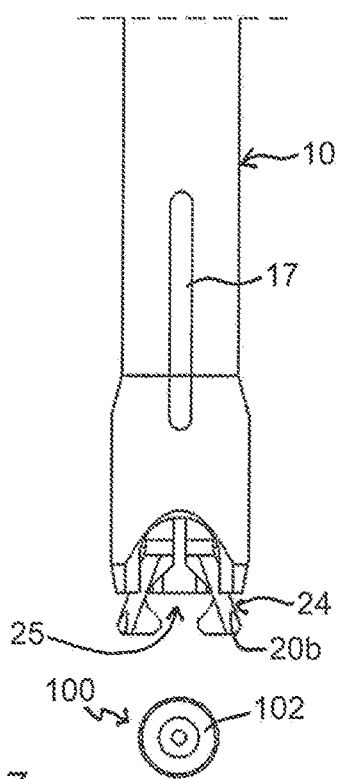
FIG. 17 shows a front view of the rod and the rod insertion device of FIGS. 15 and 16 in a direction along the rod axis, seen from an end of the rod opposite to the connection portion.

The outer sleeve 10 is shown in detail in FIGS. 12 to 14. The outer sleeve is substantially cylindrical with a central longitudinal axis $c_2$, and has two opposite transverse holes 11 at a distance from the rear end 10a for receiving the pins 35. Adjacent to the front end 10b, a housing section 12 is formed that is configured to receive the rod engagement portion 24 of the rod holding member 20 therein. The housing section 12 has a substantially U-shaped recess 13 configured to receive part of the main portion 100c of the rod 100. Inside the housing section 12, there is a cavity 14 sized to receive the rod engagement portion 24. Specifically, the cavity 14 has outwardly tapered sidewalls 14a configured to engage the outwardly tapered surface 26 of the rod engagement portion 24. Opposite to the recess 13 in a direction transverse to the longitudinal axis $c_2$, a shallow axial recess 15 is formed in the inner wall of the housing section 12 to accommodate the end portion of the connection portion 101. The length of the cavity 14 in the direction of the longitudinal axis l of the connection portion is such that when the rod engagement portion 24 has engaged the connection portion 101, the flat end 104 extends into the axial recess 15 while the U-shaped recess 13 is placed over the main portion 100c of the rod 100, as can be seen in FIG. 20.

The outer width of the housing section 12 may increase towards the front end 10b in the direction of the rod. To reduce material and save space, the width of the housing section 12 in a direction perpendicular to the rod may be smaller. For example, flat side portions 12a are formed on opposite sides to the left and to the right of the rod recess 13 and the backside opposite to the rod recess 13. In this embodiment, the width of the housing section 12 perpendicular to the rod may be greater than the width of a rod channel of a bone anchor. Lastly, a longitudinal slot 17 may extend from a main portion of the outer sleeve 10 to the housing section 12, which serves for cleaning purposes, for example.

The connection between the rod 100 and the rod insertion device will be described, referring to FIGS. 15 to 22. First, as shown in FIGS. 15 to 18, the rod holding member 20 is in the release/insert configuration. In this configuration, the engagement portion 24 projects with at least a portion of the cavity 25 out of the housing section 12. The engagement portion 24 is oriented such that a longitudinal axis of the cavity 25 is aligned or is parallel to a longitudinal channel axis of the rod recess 13. The tapered inner surfaces 14a do not engage the tapered outer surface 26 of the engagement portion 24 as shown in FIG. 18. The rod 100 is oriented with the connection portion 101 in such a way with respect to the rod insertion device that the upper pair of long sides a faces towards the front end 20b of the rod holding member 20. The marking 103 on the surface of the rod main portion 100c facilitates proper orientation of the connection portion 101.

Next, the connection portion 101 is inserted into the cavity 25. Due to the flexibility of the arms 23, the connection portion 101 can snap into the cavity 25. Thereafter, the rod holding member 20 is retracted within the outer sleeve 10 by pivoting the bracket 41 into the lock position. Through the relative movement of the rod holding member 20 and the outer sleeve, the tapered inner surface portions 14a of the housing section 12 engage the tapered outer surface portions 26 of the engagement portion 24, thereby compressing the arms 23. By means of this, the cavity 25 closes firmly around the connection portion 101 to fix the rod to the rod insertion device.

When the rod 100 is engaged by the rod holding member 20, the rod extends substantially perpendicular to the central longitudinal axis of the outer sleeve 10, but in an opposite direction to the handle portion 31.

The parts and portions of the rod insertion device and of the rod may be made of any material, preferably however, of titanium or stainless steel or of any bio-compatible metal or metal alloy or plastic material. For bio-compatible alloys, a NiTi alloy, for example Nitinol, may be used. Other materials that can be used are, for example, magnesium or magnesium alloys. Bio-compatible plastic materials that can be used may be, for example, polyether ether ketone (PEEK) or poly-L-lactide acid (PLLA). The parts can be made of the same or of different materials from one another.

Use of the rod insertion device will be explained, with reference to FIGS. 23 to 26. The figures show vertebrae 500 with bone anchors in the form of pedicle screws 300 inserted into the pedicles of the vertebrae 500. The bone anchors 300 have an anchoring section for anchoring in the bone and a receiving part 301 that may be polyaxially or monoaxially connected to the anchoring section. The receiving part 301 has a channel for placing the rod therein. Extended tabs 302 may be provided that extend the walls of the rod channel of the receiving part 301. Each receiving part 301 includes two extended tabs 302 that provide guidance for the rod when the rod is inserted into the rod channel of the receiving part 301, and also for other instruments and parts used at the implantation site.

Figure 23:
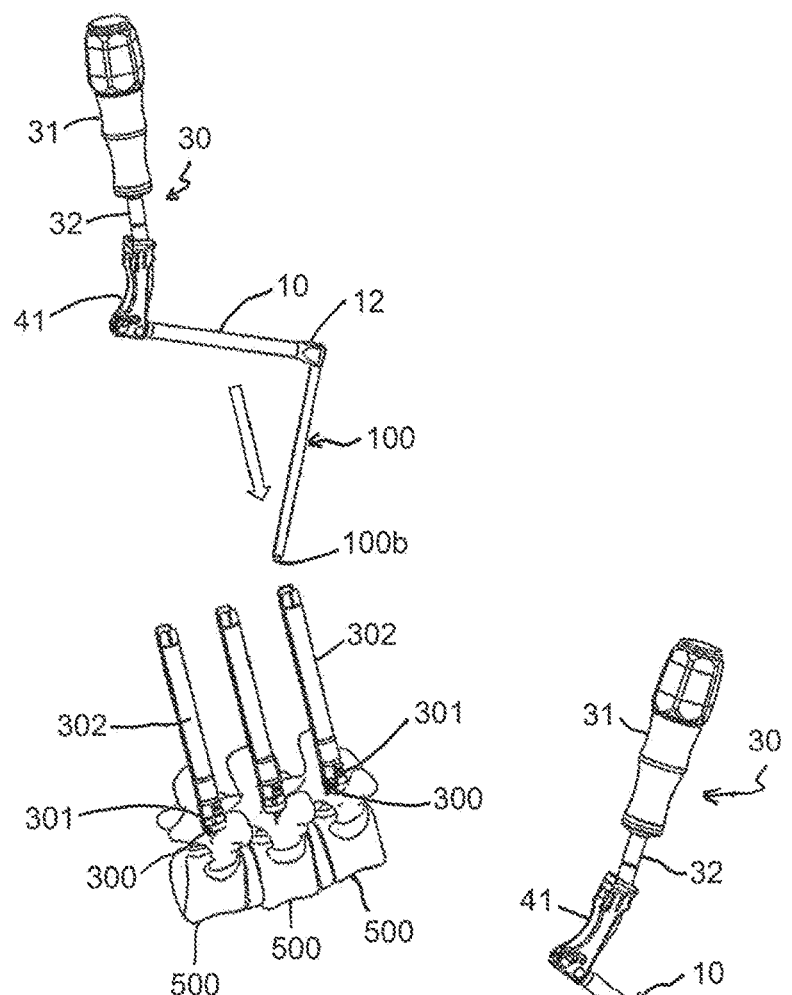
FIGS. 23 to 26 show steps of inserting the rod of FIG. 3 with the rod insertion device of FIGS. 1 and 2, and steps of subsequent removal of the rod insertion device.
Figure 24:
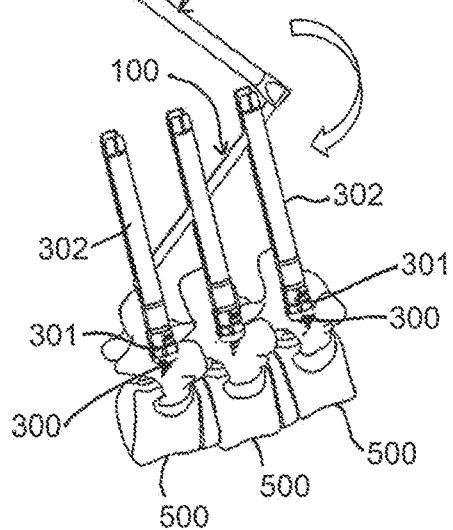
Figure 25:
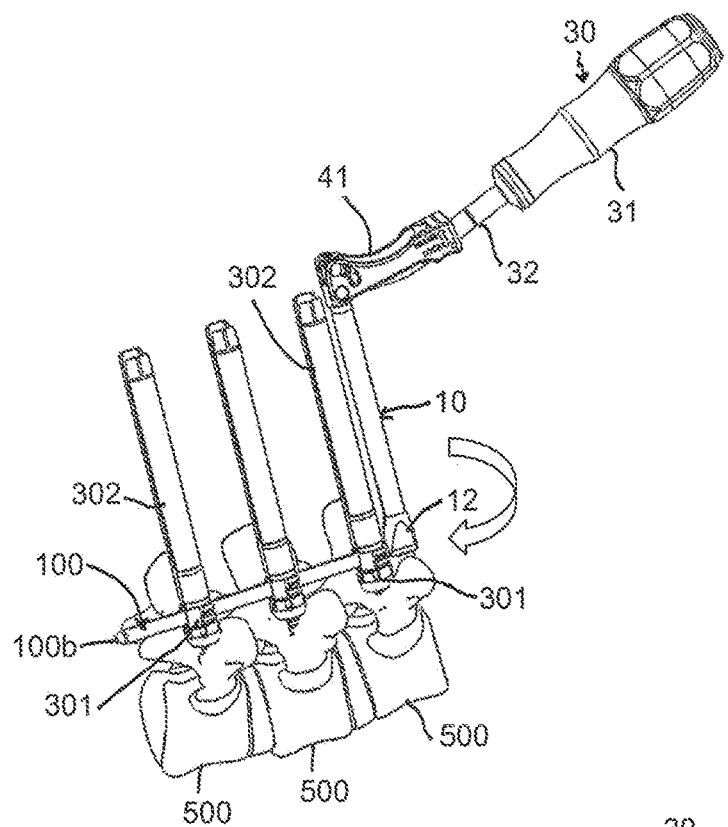

First, the rod 100 is engaged by the rod holding member 20 of the rod insertion device and locked by moving the bracket 41 into the lock position. As depicted in FIG. 23, the rod 100 is then inserted between the extended tabs 302 of one of the outermost bone anchors 300 and through the extended tabs 302 of the other bone anchors 300. Tilting the rod insertion device towards the bone anchors 300 as shown in FIG. 24 moves the rod into the rod channels until the rod rests on the bottom of the rod channels, as depicted in FIG. 25. Since the width of the housing section 12 of the outer sleeve 10 in this embodiment is greater than the width between the extended tabs 302, the housing section 12 cannot enter between the extended tabs 302.

Figure 26:
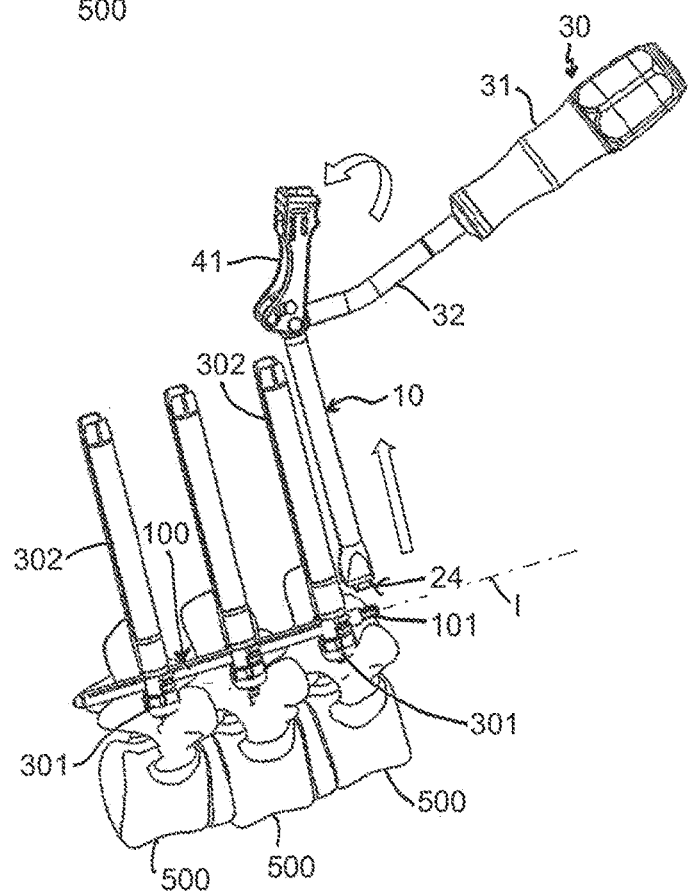

Then, the rod insertion device can be removed. As illustrated in FIG. 26, the bracket 41 is pivoted away from the handle 30 into the release position, which displaces the rod holding member 20 with respect to the outer sleeve 10 so that the rod holding cavity 25 is opened and the rod insertion device can be disengaged from the rod. The direction of removal of the rod insertion device is substantially vertical, i.e., substantially perpendicular to the rod axis and parallel to the extended tabs 302. Because the rod insertion device can be removed vertically, only little space in the direction of the rod axis is required. Thus, the rod insertion device and the rod may be advantageously used in MIS, since the necessary incisions can be kept small and the vertical movement during removal facilitates use of the device. However, the rod and the rod insertion device can also be applied in open surgery to permit a precise orientation and placement of the rod.

Figure 27:
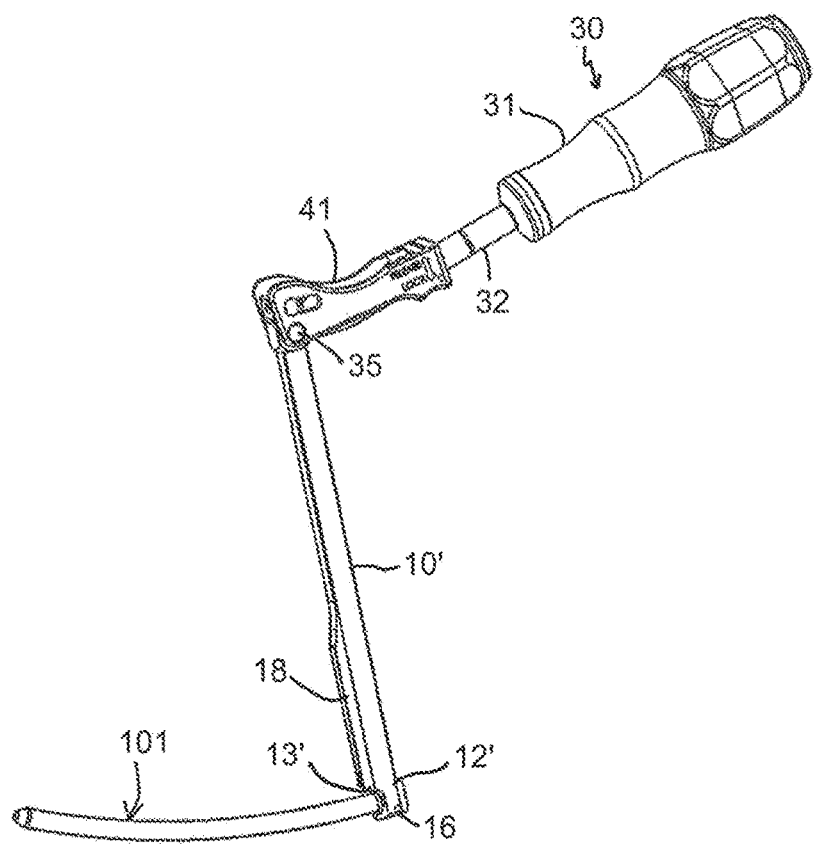
FIG. 27 shows a perspective view of a second embodiment of a rod insertion device and the rod of FIG. 4.
Figure 28:
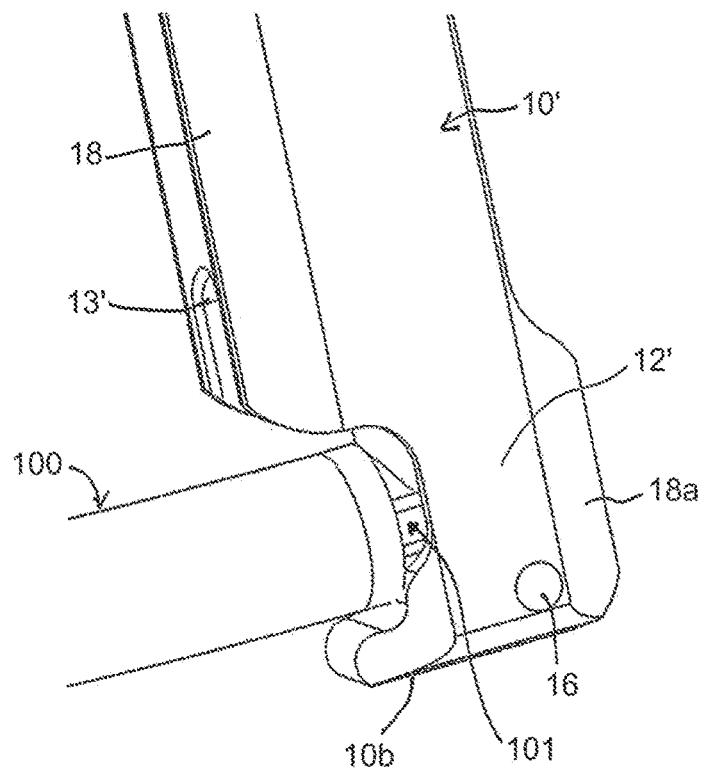
FIG. 28 shows an enlarged portion of FIG. 27.

Referring to FIGS. 27 to 38g a second embodiment of the rod insertion device will be described. Parts and portions of the second embodiment that are identical or similar to those of the first embodiment are marked with the same reference numerals, and the descriptions thereof will not be repeated. The second embodiment of the rod insertion device is shown together with the curved rod 100' as described in FIG. 4. The rod insertion device according to the second embodiment differs from the rod insertion device according to the first embodiment in the shaped of the outer sleeve and the rod holding member. As shown in FIGS. 27 and 28, the handle 30 and the displacement mechanism 40 are substantially the same as in the first embodiment. However, any other handle portion or displacement mechanism also can be used in other embodiments.

Figures 29, 30:
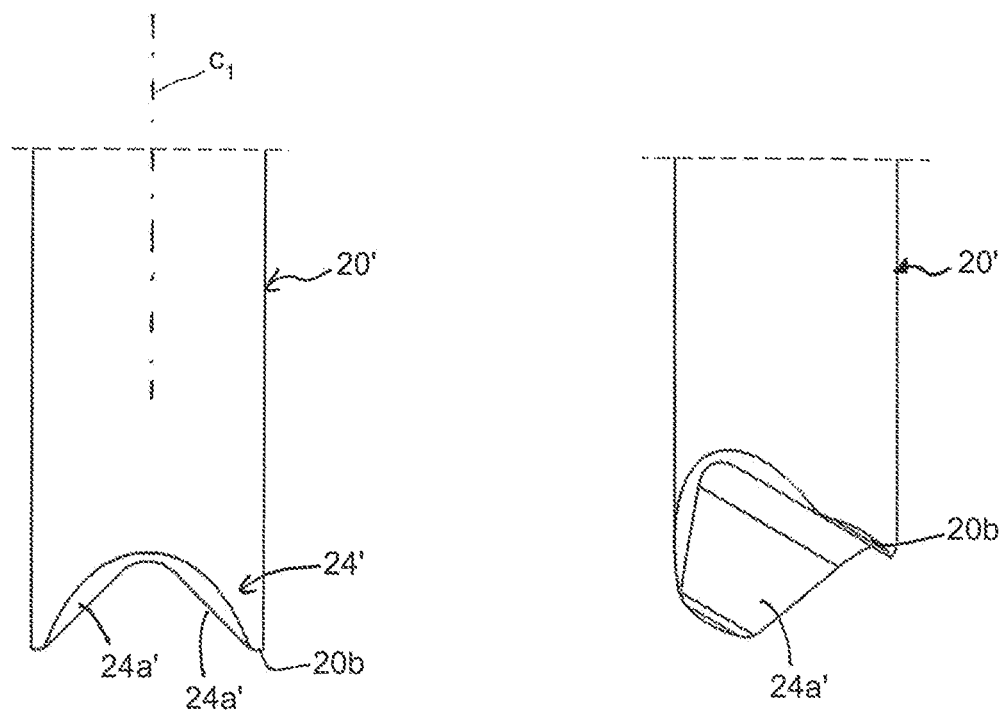
FIG. 29 shows a side view of a rod holding member of the rod insertion device according to the second embodiment shown in FIGS. 27 and 28.
FIG. 30 shows a perspective view from a bottom of the rod holding member of FIG. 29.
Figure 31:
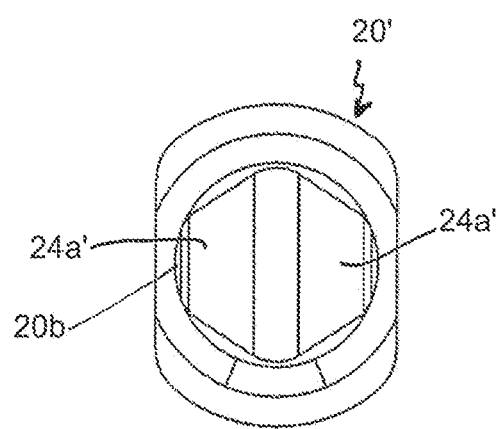
FIG. 31 shows a bottom view of the rod holding member of FIGS. 29 and 30.
Figure 32:
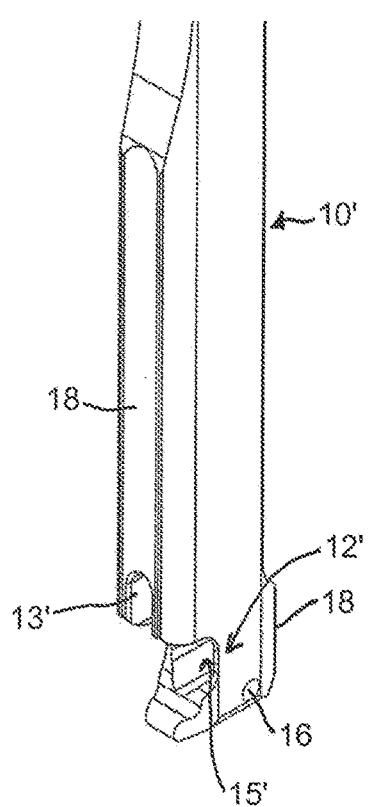
FIG. 32 shows a perspective view from a top of a portion of an outer sleeve of the rod insertion device of FIGS. 27 and 28.
Figure 33:
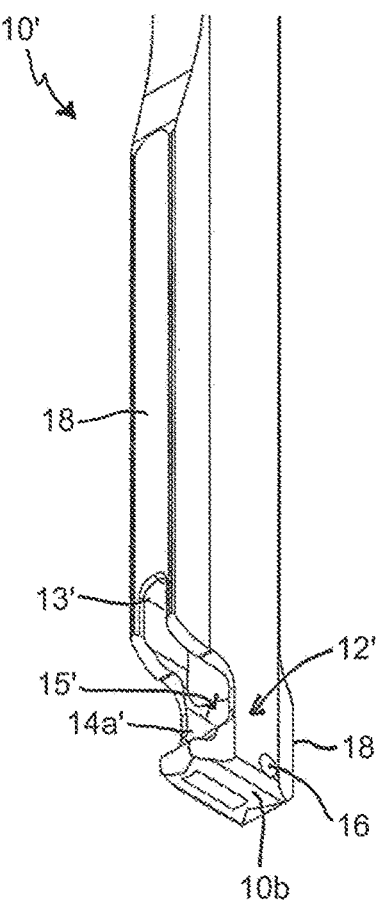
FIG. 33 shows a perspective view from a bottom of the outer sleeve of FIG. 32.

The outer sleeve 10' in this embodiment cooperates with the rod holding member 20' to hold and fix the rod. As shown in FIG. 28, a lower portion of the outer sleeve 10' includes a housing section 12' that extends below the connection portion 101 and forms a part of a rod holding cavity. Referring to FIGS. 29 to 31, the rod holding member 20' is rod-shaped with a substantially constant outer diameter. Adjacent to the front end 20b, a rod engagement portion 24' is formed which is a substantially V-shaped recess with a longitudinal axis transverse to the central longitudinal axis $c_1$ of the rod holding member 20'. The V-shaped recess is adapted to the shape of the upper portion of the connection portion 101 of the rod, and includes two sidewalls 24a' that form an angle of substantially 90°, corresponding to the upper pair of adjacent long sides a of the connection portion 101. The junction between the two sidewalls 24a' may be rounded corresponding to the rounded edge between the long sides a of the connection portion 101. Thus, the rod engagement portion 24' is configured to engage the connection portion 101 and to press onto the connection portion from above. This results in a form-fit connection between the rod holding member and the connection portion 101 with respect to a rotation of the connection portion around the longitudinal axis l.

Referring to FIGS. 32 to 37, the outer sleeve 10' may have a substantially rectangular outer contour in an upper part which may extend over half of the total length adjacent to the rear end 10a. Adjacent to the front end 10b, the housing section 12' includes a hollow receiving section 15' with a bottom 15a that is configured to engage the connection portion 101 from below. On the inner wall of the bottom 15a of the housing section 12, two inclined sidewalls 14a' form an angle of substantially 90° to receive the lower pair of long sides a of the connection portion 101 that are opposite to the upper pair of longs sides a that are engaged by the engagement portion 24' of the rod holding member 20'. A rear section 15b of the receiving section 15' may be formed to receive the end portion of the connection portion 101. Furthermore, in the bottom 15a, a transverse pin 16 is supported which extends perpendicular to the central longitudinal axis $c_2$ of the outer sleeve 10' and which projects into the receiving section 15' at a position corresponding to the recess 106 of the connection portion 101 for engaging the recess 106. Once the rod holding member 20' is pressed onto the connection portion 101, the connection portion 101 is locked between the rod engagement portion 24' of the rod holding member 20' and the inclined sidewalls 14a' of the receiving section 15' of the outer sleeve 10'. The transverse pin 16 engages the recess 106 and prevents axial movement of the connection portion 101 in the direction of its longitudinal axis l.

The width of the outer sleeve 10' in a direction perpendicular to the longitudinal axis l of the connection portion is preferably smaller than the width between the sidewalls of the rod channel of the bone anchors 300 or smaller than the distance between the extended tabs 302. By means of this, it is possible to guide the outer sleeve 10' through the extended tabs 302 of the receiving part 301.

Figure 34:
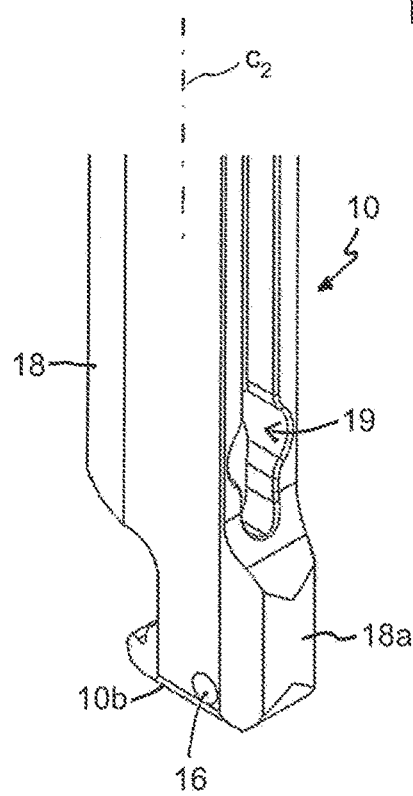
FIG. 34 shows a perspective view from a top of a portion of the outer sleeve of FIGS. 32 and 33 in a rotated position around a central longitudinal axis of the outer sleeve.
Figure 35:
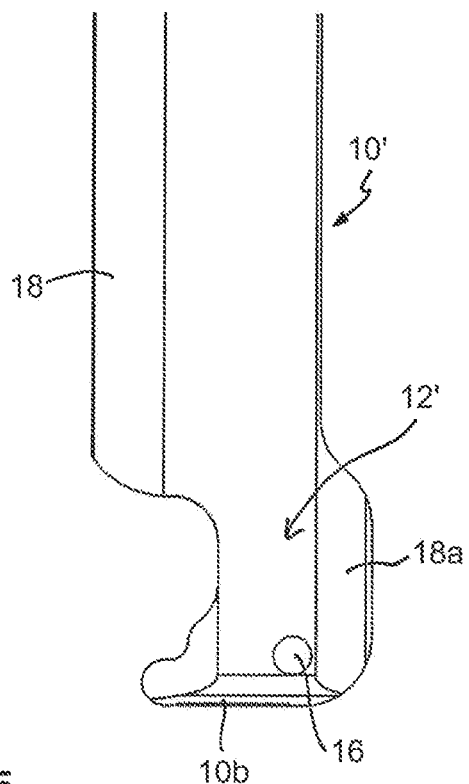
FIG. 35 shows a side view of the portion of the outer sleeve of FIGS. 32 to 34.
Figure 36:
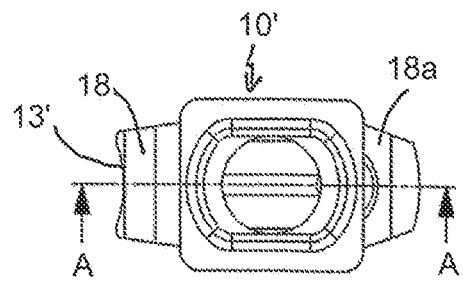
FIG. 36 shows a top view onto the outer sleeve of FIGS. 32 to 35.
Figure 37:
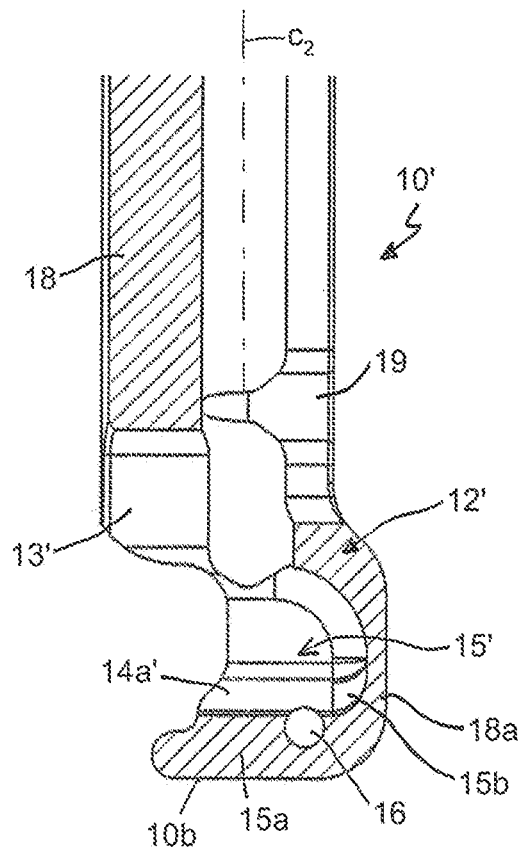
FIG. 37 shows a cross-sectional view of the portion of the outer sleeve of FIGS. 32 to 36, the cross-section taken along line A-A in FIG. 36.

Above the receiving section 15', the outer sleeve 10' includes a thickened portion 18 on a side of the rod 100'. At a lowermost section of the thickened portion 18, a substantially U-shaped recess 13' is formed in the housing section 12' that is open towards the rod and permits the rod 100' to extend therethrough. Referring specifically to FIGS. 34 and 37, on the opposite side of the thickened portion 18 in the direction of the longitudinal axis l of the connection portion 101, the housing section 12' may have a protruding portion 18a. Furthermore, above the protruding portion 18a, an axial opening 19 may be provided, for example, for manufacturing the contour of the inside of the housing 12' and/or for facilitating cleaning.

Figures 38A, 38B, 38C, 38D:
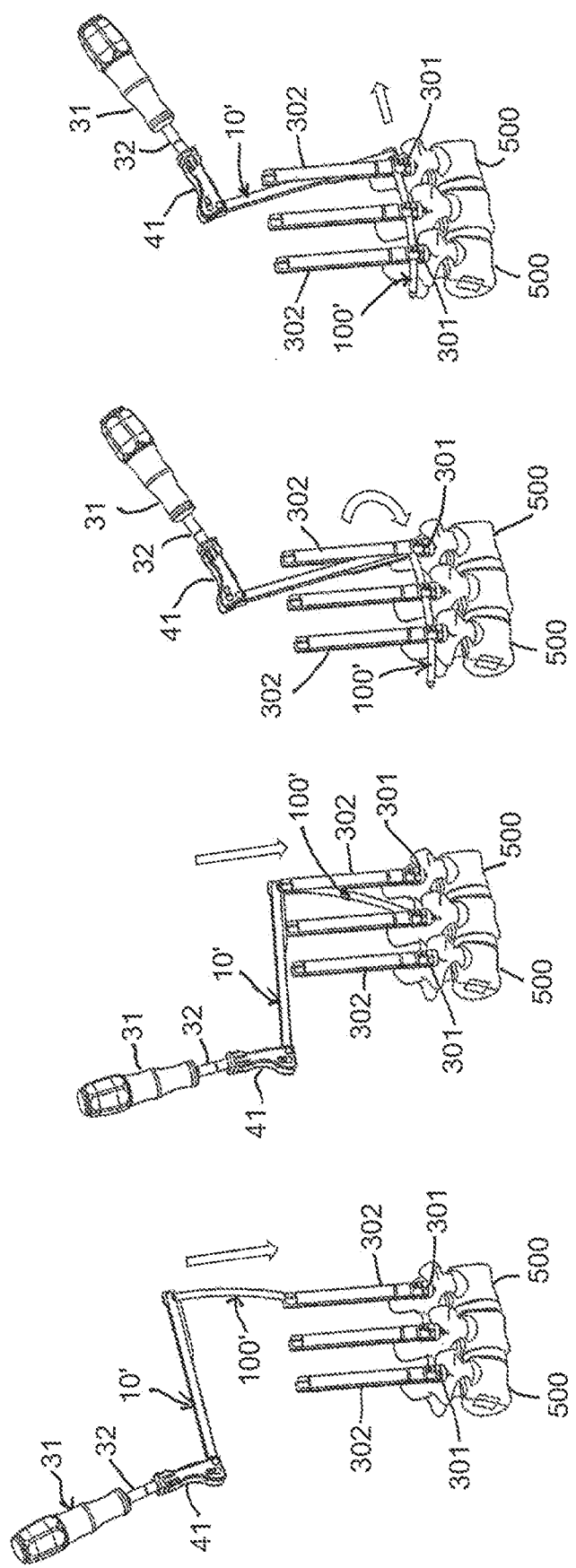
FIGS. 38a to 38g show steps of insertion of the rod of FIG. 4 with the rod insertion device of FIGS. 27 and 28, and subsequent removal of the rod insertion device.

Referring now to FIGS. 38a to 38c, the insertion of the rod 100' will be described. First, the rod 100' is fixed to the rod insertion device by inserting the connection portion 101 into the receiving section 15', so that the transverse pin 16 engages the recess 106 of the connection portion 101. Then, the rod holding member 20' is moved downward by tilting the bracket 41 into the lock position. The engagement portion 24' engages the connection portion 101 and presses it against the tapered sidewalls 14a' at the bottom of the receiving section 15 to clamp and finally fix the rod at the connection portion 101. The rod 100' is then inserted through the insertion corridor prepared by MIS and guided through the extended tabs 302 of each of the bone anchors 300, as illustrated in FIGS. 38a and 38b. Thereafter, the rod insertion device is tilted such that the rod 100' can be placed into the rod channel of the receiving parts 301 of the bone anchors 300, respectively, as shown in FIG. 38c.

Figure 38E:
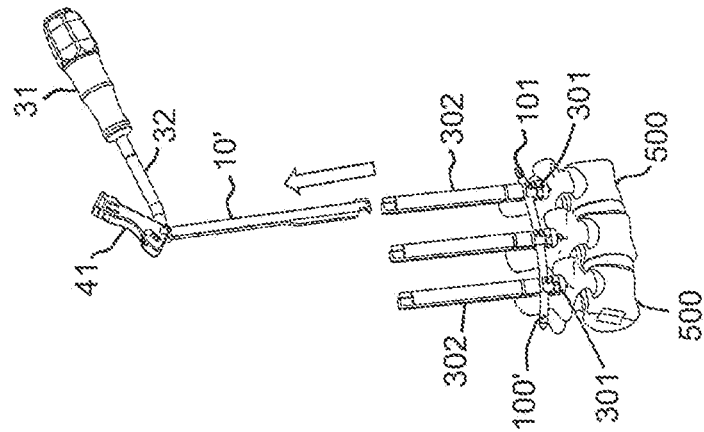
Figure 38F:
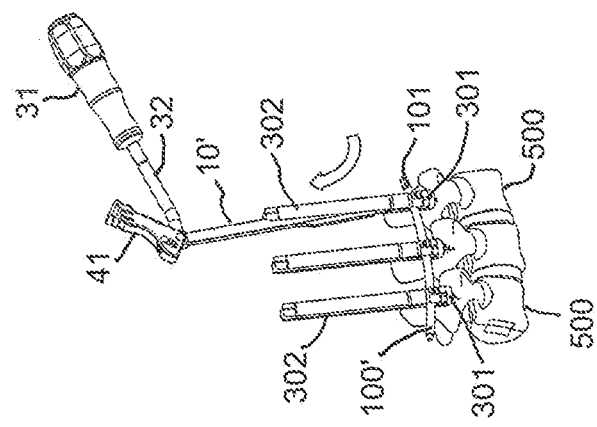
Figure 38G:
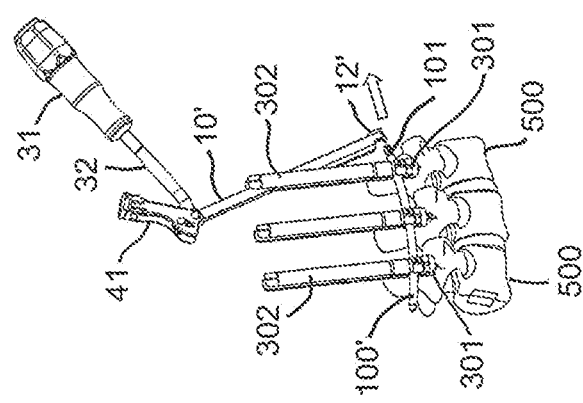

Next, as shown in FIG. 38d, the rod 100' may be moved to a small extent in the direction of the longitudinal axis l of the connection portion 101 behind the outermost one of the bone anchors. Then as shown in FIG. 38e, the bracket 41 is pivoted into the release position and the rod is released. Thereafter, the rod insertion device can be removed by tilting it and moving it between the extended tabs 302 (FIG. 38f), and thereafter retracting it vertically, i.e., substantially parallel to the extended tabs 302 (FIG. 38g). Hence, also in this case, the necessary space for removing the rod insertion device is minimal.

When the curved rod 100' is intended be placed with the curvature facing in the opposite direction, the rod 100' can be rotated by 180° around the longitudinal axis of the connection portion 101 and inserted into the receiving section 15' of the outer sleeve 10' so that the opposite one of the recesses 106 can be engaged by the pin 16. Hence, it is possible to easily orient the rod to be used in an appropriate or otherwise desired manner with the aid of the rod insertion device.

Figure 39:
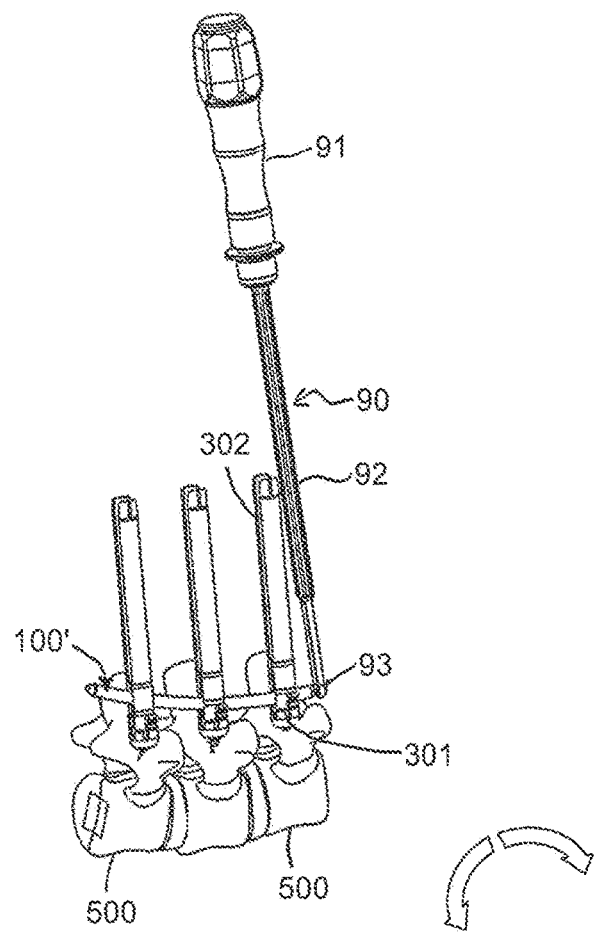
FIG. 39 shows a perspective view of a step of attaching another instrument, such as a driver, to a rod when the rod has already been inserted into the rod channel of bone anchors.
Figure 40:
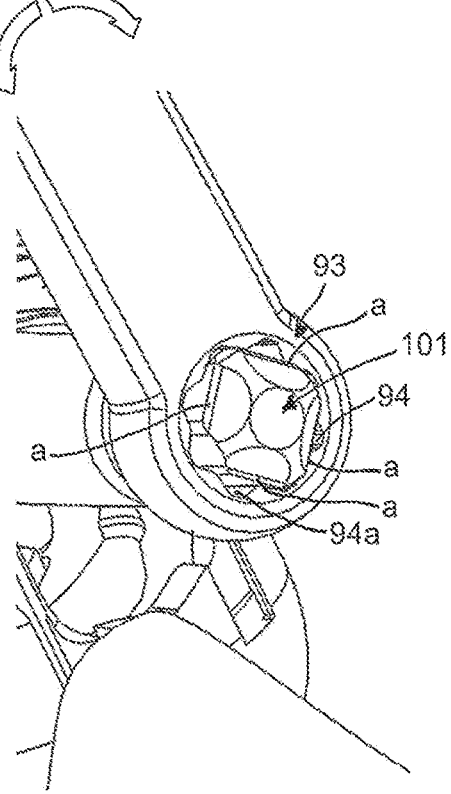
FIG. 40 shows a perspective view from a front of a portion of the attachment of the further instrument to the rod.

Referring to FIGS. 39 and 40, the use of a further instrument together with the rod 100' is shown. It shall be mentioned that the curved rod 100' is shown only as an example, and any other rod, such as the straight rod 100 and/or other rods can be used. The instrument 90 as shown in the figures may be used to rotate the rod 100' once the rod has been placed into the rod channel of the receiving parts 301 of the bone anchors 300. The instrument 90 may be, for example, a ring wrench that includes a handle 91, a shaft 92, and an engagement portion 93 at the end of the shaft 92 for engaging the connection portion 101. The engagement portion 93 has a ring-shaped opening 94 that is configured to encompass the connection portion 101. The ring-shaped opening 94 has axial grooves 94a arranged in a star-like manner at regular distances, in the embodiment eight grooves, that permit the edge between a pair of long sides a of the polygonal outer contour of the connection portion 101 to extend therein. With such a structure, the engagement portion 101 can be engaged by the instrument at discrete positions of 45° around the longitudinal axis 1 of the connection portion 101. Hence, the rod can be rotated with the instrument in either direction to assume a suitable position using the instrument.

Other instruments (not shown) may also be attached to the connection portion to manipulate the rod once the rod is inserted into the rod channel. For example, it is also conceivable to just hold the rod in place with a rod holder during manipulation of the bone anchors.

Further modifications of the above-described embodiments are also conceivable. The particular features, structures, or characteristics of one embodiment may also be combined with the other embodiments in any suitable manner to produce a multiplicity of further embodiments. Particular shapes of the elements are not limited to the specific shapes shown in the drawings, but may also vary.

Since the connection portion is independent of the shape of the rod, any rod shape may be used. For example, the rod can have a cross-section other than a circular cross-section. The rod may have various shapes and/or varying cross-sections along its length. Moreover, the connection portion can be present on both ends of the rod. The connection portion may also have another polygonal contour.

For the bone anchor, all types of bone anchors that are suitable for anchoring in bone or vertebra and configured to be connected to a rod, for example, in a monoaxial or a polyaxial manner may be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A system for spine surgery comprising:
 a rod comprising a longitudinal axis and a connection portion at one end; and
 a rod insertion device comprising a rod holding member, the rod holding member comprising a central axis and a rod engagement portion at one end, wherein the connection portion of the rod is movable along the central axis from a position outside the rod engagement portion into the rod engagement portion while the longitudinal axis of the rod is arranged transversely relative to the central axis, and wherein at least part of a shape of the rod engagement portion substantially matches at least part of a shape of the connection portion of the rod to engage the connection portion in a fixed manner at more than one distinct rotational orientation around the longitudinal axis;

wherein when the connection portion is engaged with the rod engagement portion, when viewed in a plane perpendicular to the longitudinal axis of the rod, a cross-section of the connection portion has a maximum height measured in a direction of the central axis of the rod holding member that is greater than a maximum width of the connection portion measured in a direction transverse to the longitudinal axis.

2. The system of claim 1, wherein the connection portion is engageable by the rod engagement portion in a form-fit manner to restrict the relative rotation therebetween.

3. The system of claim 1, wherein the cross-sectional shape of the connection portion is substantially polygonal.

4. The system of claim 1, wherein sides of the cross-sectional shape of the connection portion converge in the direction of the central axis of the rod holding member to define the maximum height of the cross-section.

5. The system of claim 1, wherein the cross-sectional shape of the connection portion comprises at least four equal long sides that are arranged in a diamond-shaped envelope, with two opposite corners of the diamond-shaped envelope arranged in a direction parallel to the central axis of the rod holding member.

6. The system of claim 5, wherein the cross-sectional shape of the connection portion further comprises two short sides that are shorter than the long sides and that separate upper and lower pairs of the long sides from one another to form a hexagonal shape.

7. The system of claim 1, wherein the connection portion defines at least one recess, and wherein the rod insertion device further comprises a protrusion configured to engage the recess.

8. The system of claim 7, wherein the at least one recess is a first recess, and wherein the connection portion defines a second recess at an end of the connection portion opposite the first recess, such that the first and second recesses are selectively engageable by the protrusion of the rod insertion device to define two fixed rotational orientations of the connection portion relative to the rod engagement portion.

9. The system of claim 1, wherein the rod insertion device further comprises an outer sleeve positionable around and movable axially relative to the rod holding member between a holding position to a release position.

10. The system of claim 9, wherein the rod engagement portion comprises at least two arms that define a rod holding cavity therebetween, and wherein the arms are movable laterally relative to one another between a holding position to hold the connection portion and a release position to insert and remove the connection portion.

11. The system of claim 10, wherein the rod holding cavity is configured to enclose the connection portion of the rod from two opposite sides in a direction of the longitudinal axis.

12. The system of claim 9, wherein the rod engagement portion of the rod holding member and the outer sleeve together define a rod holding cavity for holding the connection portion of the rod.

13. The system of claim 1, further including a bone anchor with a shank for anchoring in bone and a receiving part comprising two legs that define a channel for the rod.

14. The system of claim 13, wherein the rod insertion device has a lateral width that is smaller than a distance between the two legs of the bone anchor.

15. The system of claim 13, wherein the rod insertion device has a lateral width that is greater than a distance between the two legs of the bone anchor.

16. A system for spine surgery comprising:
a rod comprising a longitudinal axis and a connection portion at one end; and
a rod insertion device comprising a rod holding member, the rod holding member comprising a central axis and a rod engagement portion at one end, wherein the connection portion of the rod is movable along the central axis from a position outside the rod engagement portion into the rod engagement portion while the longitudinal axis of the rod is arranged transversely relative to the central axis, and wherein the rod engagement portion is configured to engage the connection portion in a fixed manner at only two distinct rotational orientations that are rotated 180° around the longitudinal axis from one another.

17. The system of claim 16, wherein the rod insertion device comprises a protrusion that is configured to selectively engage respective recesses that are located 180° around the longitudinal axis from one another on the connection portion.

18. A rod for spine surgery comprising:
a longitudinal axis;
a connection portion at one end that is engageable with a rod insertion device, wherein when viewed in a plane perpendicular to the longitudinal axis, a cross-section of the connection portion forms a shape that comprises at least four equal long sides that are arranged in a diamond-shaped envelope, with two opposite corners of the diamond-shaped envelope arranged along a first direction, the shape having a maximum height measured in the first direction that is greater than a maximum width measured in a direction transverse to the first direction; and
a first recess and a second recess formed on opposite sides of the connection portion along the first direction, wherein the first and second recesses are configured to be selectively engaged by a protrusion of the rod insertion device to hold the rod to the rod insertion device.

19. The rod of claim 18, wherein the first and second recesses have substantially the same shape, and wherein the connection portion does not have any further recesses having substantially the same shape as the first and second recesses.

20. The rod of claim 18, wherein the shape of the cross-section of the connection portion is substantially polygonal, and wherein the long sides converge in the first direction to define the maximum height of the connection portion.

21. The rod of claim 18, wherein the cross-sectional shape of the connection portion further comprises two short sides that are shorter than the long sides and that separate upper and lower pairs of the long sides from one another to form a hexagonal shape.

* * * * *